United States Patent [19]

Elbe et al.

[11] Patent Number: 4,968,712

[45] Date of Patent: Nov. 6, 1990

[54] FUNGICIDAL 1,4-DISUBSTITUTED 1-AZOLYL-3,3-DIMETHYLBUTANE DERIVATIVES

[75] Inventors: Hans-Ludwig Elbe, Wuppertal; Albrecht Marhold, Leverkusen; Karl H. Büchel, Burscheid; Stefan Dutzmann, Duesseldorf; Paul Reinecke, Leverkusen; Wilhelm Brandes, Leichlingen; Gerhard Hänssler, Leverkusen, all of Fed. Rep. of Germany

[73] Assignee: Bayer Aktiengesellschaft, Leverkusen, Fed. Rep. of Germany

[21] Appl. No.: 225,971

[22] Filed: Jul. 29, 1988

[30] Foreign Application Priority Data

Jul. 31, 1987 [DE] Fed. Rep. of Germany ....... 3725397

[51] Int. Cl.$^5$ ................ A01N 43/653; C07D 249/08
[52] U.S. Cl. .................................. 514/383; 514/184; 548/101; 548/267.8; 548/268.6
[58] Field of Search ................... 548/101, 262, 267.8, 548/268.6; 514/184, 383

[56] References Cited

U.S. PATENT DOCUMENTS

| | | | |
|---|---|---|---|
| 4,549,900 | 10/1985 | Krämer et al. | 71/92 |
| 4,551,469 | 11/1985 | Parry et al. | 548/262 |
| 4,734,126 | 3/1988 | Holmwood et al. | 71/76 |

FOREIGN PATENT DOCUMENTS

| | | |
|---|---|---|
| 0100952 | 2/1984 | European Pat. Off. |
| 0175233 | 3/1986 | European Pat. Off. |
| 0226916 | 7/1987 | European Pat. Off. |
| 3544731 | 6/1987 | Fed. Rep. of Germany |
| 0054865 | 6/1982 | United Kingdom |

*Primary Examiner*—Glennon H. Hollrah
*Assistant Examiner*—Patricia L. Morris
*Attorney, Agent, or Firm*—Sprung Horn Kramer & Woods

[57] ABSTRACT

Fungicidal 1,4-disubstituted 1-azolyl-3,3-dimethylbutane derivatives of the formula $$R^5 \quad R^1 \quad\quad CH_3 \quad R^6$$
$$R^4-\text{benzene ring}-CH_2-\underset{CH_3}{\overset{}{C}}-A-\underset{\underset{N\diagup\!\!\!\diagdown N}{}}{\overset{}{C}}-R^7$$
$$R^3 \quad R^2$$

(I)

in which
R$^1$ represents hydrogen or halogen,
R$^2$ represents hydrogen or halogen,
R$^3$ represents hydrogen, halogen or trifluoromethoxy,
R$^4$ represents halogen, trifluoromethoxy, trifluoromethylthio, trifluoromethylsulphinyl, trifluoromethylsulphonyl, difluoromethoxy, difluorochloromethoxy, trifluorochloroethoxy, tetrafluoroethoxy, trifluoroethoxy, difluoromethylthio, trifluorochloroethylthio, tetrafuoroethylthio, difluoromethylsulphinyl, difluorochloromethylsulphinyl, trifluorochloroethylsulphinyl, tetrafluoroethylsulphinyl, difluoromethylsulphonyl, difluorochloromethylsulphonyl, trifluorochloroethylsulphonyl, tetrafluoroethylsulphonyl, difluorobromomethylthio, difluorobromomethylsulphinyl, difluorobromomethylsulphonyl or difluorochloromethylthio or
R$^3$ and R$^4$ together represent alkylenedioxy substituted by halogen,
R$^5$ represents hydrogen or halogen,
A represents a keto group or a CH(OH) grouping,
Z represents a nitrogen atom or the CH group and
R$^6$ and R$^7$ identical or different and independently of one another represent hydrogen, alkyl, alkenyl, alkynyl, optionally substituted cycloalkyl, optionally substituted cycloalkylalkyl or optionally substituted phenylalkyl, where
R$^3$ represents trifluoromethoxy when
R$^4$ represents halogen, and addition products thereof with acids and metal salts.

10 Claims, No Drawings

FUNGICIDAL 1,4-DISUBSTITUTED 1-AZOLYL-3,3-DIMETHYLBUTANE DERIVATIVES

The present invention relates to new 1,4-disubstituted 1-azolyl-3,3-dimethylbutane derivatives, several processes for their preparation and their use as fungicides.

It has already been disclosed that numerous azolylcarbonyl and azolylcarbinol derivatives possess fungicidal properties (compare U.S. Patent Specification No. 4,549,900, EP-OS (European Published Specification) No. 0,054,865 and EP-OS (European Published Specification) No. 0,055,833 and DE-OS (German Published Specification) No. 3,544,731). 1-(4-Chlorophenyl)-2,2-dimethyl-4-(1,2,4-triazol-1-yl)-hexan-3-one; 1-(4-chlorophenyl)-2,2-di-methyl-4-(1,2,4-triazol-1-yl)-hexan-3-ol; 1-(3-bromo-4-fluorophenyl)-2,2-dimethyl-4-(1,2,4-triazol-1-yl)-oct-7- en-3-ol and 1-(4-methylphenyl)-2,2-dimethyl-4-(1,2,4-triazol-1-yl)-pentan-3-ol are thus employed for combating fungi. However, the action of these compounds is not always very satisfactory in certain areas of indication, in particular at low application rates and concentrations.

New 1,4-disubstituted 1-azolyl-3,3-dimethylbutane derivatives of the formula (I)

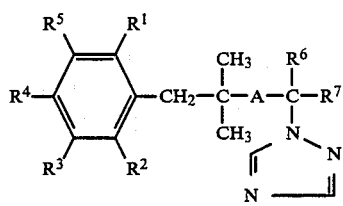

in which
$R^1$ represents hydrogen or halogen,
$R^2$ represents hydrogen or halogen,
$R^3$ represents hydrogen, halogen or trifluoromethoxy,
$R^4$ represents halogen, trifluoromethoxy, trifluoromethylthio, trifluoromethylsulphinyl, trifluoromethylsulphonyl, difluoromethoxy, difluorochloromethoxy, trifluorochloroethoxy, tetrafluoroethoxy, trifluoroethoxy, difluoromethylthio, trifluorochloroethylthio, tetrafluoroethylthio, difluoromethylsulphinyl, difluorochloromethylsulphnyl,trifluorochloroethylsulphinyl, tetrafluoroethylsulphinyl, difluoromethylsulphonyl, difluorochloromethylsulphonyl, trifluorochloroethylsulphonyl, tetrafluoroethylsulphonyl, difluorobromomethylthio, difluorobromomethylsulphinyl, difluorobromomethylsulphonyl or difluorochloromethylthio or
$R^3$ and $R^4$ together represent alkylenedioxy substituted by halogen,
$R^5$ represents hydrogen or halogen,
A represents a keto group or a CH(OH) grouping,
Z represents a nitrogen atom or the CH group and
$R^6$ and $R^7$ are identical or different and independently of one another represent hydrogen, alkyl, alkenyl, alkinyl, optionally substituted cycloalkyl, optionally substituted cycloalkylalkyl and optionally substituted phenylalkyl, where
$R^3$ represents trifluoromethoxy when
$R^4$ represents halogen,
and also their acid addition salts and metal salt complexes, have now been found.

The compounds of the formula (I) in which A represents the CH(OH) group possess two adjacent asymmetrically substituted carbon atoms. They can therefore exist in the two geometric isomers (threo and erythro form), which can occur in various ratios. The compounds of the formula (I) in which A represents the keto group possess an asymmetrically substituted carbon atom. In both cases, the compounds of the formula (I) can exist in different optical isomeric forms, which can occur in various ratios. All isomers are claimed according to the invention.

Furthermore, it has been found that the new 1,4-disubstituted 1-azolyl-3,3-dimethylbutane derivatives of the formula (I) and their acid addition salts and metal salt are obtained when (a) halogeno-ketones of the formula

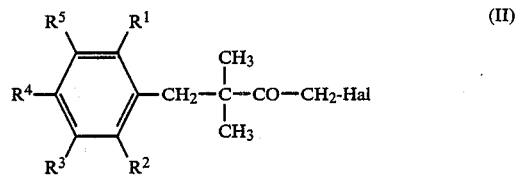

in which
$R^1$, $R^2$, $R^3$, $R^4$ and $R^5$ have the abovementioned meaning and
Hal represents halogen,
are reacted with an azole of the formula

in which
Z has the abovementioned meaning, in the presence of a diluent and in the presence of an acid-binding agent,
or
(b) ketones of the formula

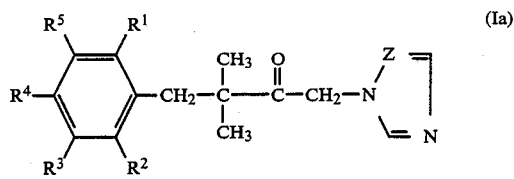

in which
$R^1$, $R^2$, $R^3$, $R^4$, $R^5$ and Z have the abovementioned meaning,
are reacted with a compound of the formula
$$R^8-Y \qquad (IV)$$

in which
$R^8$ represents alkyl, alkenyl, alkinyl, optionally substituted cycloalkyl, optionally substituted cycloalkylalkyl or optionally substituted phenylalkyl and
Y represents an electron-withdrawing leaving group,
if appropriate in the presence of an acid-binding agent and also in the presence of a diluent and if appropriate in the presence of a catalyst, (c) ketones of the formula

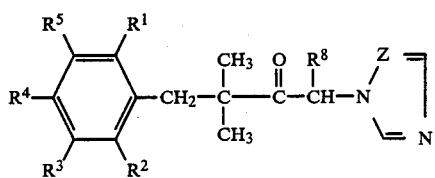

in which
R$^1$, R$^2$, R$^3$, R$^4$, R$^5$, R$^8$ and Z have the abovementioned meaning,
are reacted with a compound of the formula
$$R^9-Y^1 \quad (V)$$
in which
R$^9$ represents alkyl, alkenyl, alkinyl, optionally substituted cycloalkyl, optionally substituted cycloalkylalkyl or optionally substituted phenylalkyl and
Y$^1$ represents an electron-withdrawing leaving group, if appropriate in the presence of an acid-binding agent and also in the presence of a diluent and if appropriate in the presence of a catalyst, or (d) ketones of the formula

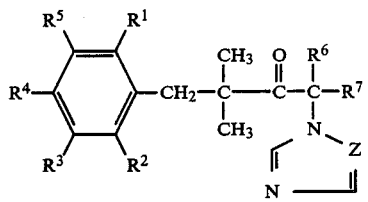

in which
R$^1$, R$^2$, R$^3$, R$^4$, R$^5$, R$^6$ and R$^7$ have the abovementioned meaning,
are reacted with a reductant if appropriate in the presence of a diluent, (e) 1,4-disubstituted 1-azolyl-3,3-dimethyl-butane derivatives of the formula

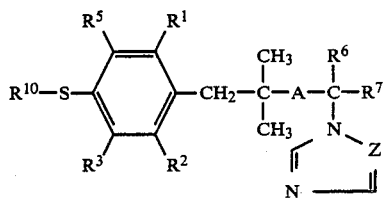

in which
R$^1$, R$^2$, R$^3$, R$^5$, R$^6$, R$^7$, A and Z have the abovementioned meaning and
R$^{10}$ represents trifluoromethyl, difluoromethyl, trifluorochloroethyl, tetrafluoroethyl, difluorochloromethyl or difluorobromomethyl,
are reacted with an oxidant, if appropriate in the presence of a diluent and if appropriate in the presence of a reaction auxiliary,
and if appropriate an acid or a metal salt is adducted to the compounds of the formula (I) thus obtained.

Finally, it has been found that the new 1,4-disubstituted 1-azolyl-3,3-dimethylbutane derivatives of the formula (I) and their acid addition salts and metal salt complexes possess very good fungicidal properties.

Surprisingly, the substances according to the invention are distinguished by a better fungicidal action than the constitutionally similar known compounds of the prior art with the same indication. The substances according to the invention thus surpass, for example, 1-(4-chlorophenyl)-2,2-dimethyl-4-(1,2,4-triazol-1-yl)-hexan-3-one; 1-(4-chlorophenyl)-2,2-dimethyl-4-(1,2,4-triazol-1-yl)-hexan-3-ol; 1-(3-bromo-4-fluorophenyl)-2,2-dimethyl-4-(1,2,4-triazol-1-yl)-oct-7-en-3-ol and 1-(4-methylphenyl)-2,2-dimethyl-4-(1,2,4-triazol-1-yl)-pentan-3-ol with respect to their fungicidal properties.

In addition, the new 1,4-disubstituted 1-azolyl-3,3-dimethyl-butan-2-ones of the formulae (Ia), (Ib), (Ic) and (Id) are important intermediates for the preparation of further plant protecting active compounds. Functional derivatives of the keto group such as, for example, oximes and oxime-ethers, hydrazones and ketals can thus be obtained by suitable reactions.

The new 1,4-disubstituted 1-azolyl-3,3-dimethyl-butan-2-ols are incidentally also important intermediates for the preparation of further plant protecting active compounds. Thus, for example, these compounds can be converted in the customary manner into the corresponding ethers by reaction at the hydroxyl group. Furthermore, acyl or carbamoyl derivatives of the alcohols of the formula (I) can be obtained in a manner which is known in principle by reaction with, for example, acyl halides or carbamoyl chlorides.

Formula (I) provides a general definition of the 1,4-disubstituted 1-azolyl-3,3-dimethylbutane derivatives according to the invention. Preferred compounds of the formula (I) are those in which
R$^1$ represents hydrogen, fluorine, chlorine or bromine,
R$^2$ represents hydrogen, fluorine, chlorine or bromine,
R$^3$ represents hydrogen, fluorine, chlorine, bromine or trifluoromethoxy,
R$^4$ represents fluorine, chlorine, bromine, trifluoromethoxy, trifluoromethylthio, trifluoromethylsulphinyl, trifluoromethylsulphonyl, difluoromethoxy, difluorochloromethoxy, trifluorochloroethoxy, tetrafluoroethoxy, trifluoroethoxy, difluoromethylthio, trifluorochloroethylthio, tetrafluoroethylthio, difluoromethylsulphinyl, difluorochloromethylsulphinyl, trifluorochloroethylsulphinyl, tetrafluoroethylsulphinyl, difluoromethylsulphonyl, difluorochloromethylsulphonyl, trifluorochloroethylsulphonyl, tetrafluoroethylsulphonyl, difluorobromomethylthio, difluorobromomethylsulphinyl, difluorobromomethylsulphonyl or difluorochloromethylthio or
R$^3$ and R$^4$ together represent a grouping of the formula

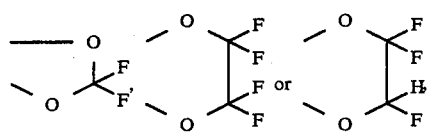

A represents a keto group or a CH(OH) grouping,
Z represents a nitrogen atom or the CH group and
R$^6$ and R$^7$ are identical or different and independently of one another represent hydrogen, straight-chain or branched alkyl having 1 to 12 carbon atoms, straight-chain or branched alkenyl or alkinyl each having 3 to 12 carbon atoms, cycloalkyl having 3 to 7 carbon atoms which is optionally monosubstituted or disubstituted by identical or different halogen and/or alkyl substituents, cycloalkylalkyl which has 3 to 7 carbon atoms in the cycloalkyl part and 1 to 4 carbon atoms in the alkyl part and is optionally monosubstituted or disubstituted by identical or different halogen and/or alkyl substituents, or optionally substituted phenylalkyl having 1 to 4 carbon atoms in the alkyl part, where phenyl substituents which may be mentioned being halogen, alkyl having 1 to 4 carbon atoms, alkoxy and alkylthio each having 1 to 4 carbon atoms, halogenoalkyl, halogenoalkoxy, halogenoalkylthio, halogenoalkylsulphinyl and halogenoalkylsulphonyl each having 1 to 4 carbon atoms and 1 to 5 identical or different halogen atoms, such as fluorine, chlorine and/or bromine atoms, nitro, cyano and alkoxycarbonyl having 1 to 4 carbon atoms in the alkoxy part, or phenyl and phenoxy which are both optionally monosubstituted to trisubstituted by identical or different fluorine, chlorine and/or bromine substituents, or two adjacent phenyl substituents together represent a grouping of the formula

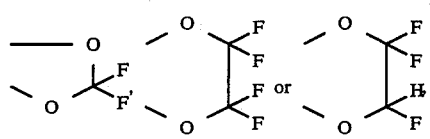

where
$R^3$ represents trifluoromethoxy, however, when
$R^4$ represents fluorine, chlorine or bromine. Particularly preferred compounds of the formula (I) are those in which
$R^1$ represents hydrogen, fluorine, chlorine or bromine,
$R^2$ represents hydrogen, fluorine, chlorine or bromine,
$R^3$ represents hydrogen, fluorine, chlorine, bromine or trifluoromethoxy,
$R^4$ represents fluorine, chlorine, bromine, trifluoromethoxy, trifluoromethylthio, trifluoromethylsulphinyl, trifluoromethylsulphonyl, difluoromethoxy, difluorochloromethoxy, trifluorochloroethoxy, tetrafluoroethoxy, trifluoroethoxy, difluoromethylthio, trifluorochloroethylthio, tetrafluoroethylthio, difluoromethylsulphinyl, difluorochloromethylsulphinyl, trifluorochloroethylsulphinyl, tetrafluoroethylsulphinyl, difluoromethylsulphonyl, difluorochloromethylsulphonyl, trifluorochloroethylsulphonyl, tetrafluoroethylsulphonyl, difluorobromomethylthio, difluorobromomethylsulphinyl, difluorobromomethylsulphonyl or difluorochloromethylthio or
$R^3$ and $R^4$ together represent a grouping of the formula

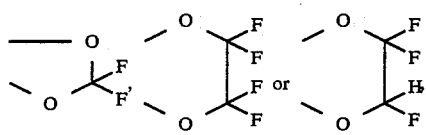

A represents a keto group or a CH(OH) grouping,
Z represents a nitrogen atom or the CH group,
$R^6$ represents hydrogen, straight-chain or branched alkyl having 1 to 7 carbon atoms, straight-chain or branched alkenyl or alkinyl each having 3 to 7 carbon atoms, cycloalkyl having 5 to 7 carbon atoms which is optionally monosubstituted or disubstituted by identical or different fluorine, chlorine and/or methyl substituents, cycloalkylalkyl which has 3 to 7 carbon atoms in the cycloalkyl part and 1 to 4 carbon atoms in the alkyl part and is optionally monosubstituted or disubstituted by identical or different fluorine, chlorine and/or methyl substituents, or phenylalkyl having 1 or 2 carbon atoms in the alkyl part, it being possible for the phenyl part to be monosubstituted to trisubstituted by fluorine, chlorine, bromine, methyl, ethyl, n-propyl, tert.-butyl, methoxy, ethoxy, methylthio, ethylthio, trifluoromethyl, trifluoromethoxy, trifluoromethylthio, trifluoromethylsulphinyl, trifluoromethylsulphonyl, nitro, cyano, methoxycarbonyl, ethoxycarbonyl, phenyl which is optionally substituted by fluorine and/or chlorine, and/or phenoxy which is optionally substituted by fluorine and/or chlorine, or by two adjacent substituents which together represent a grouping of the formula

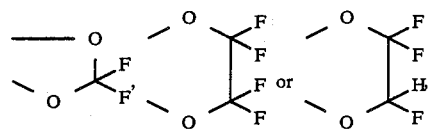

and
$R^7$ represents hydrogen, straight-chain or branched alkyl having 1 to 7 carbon atoms, straight-chain or branched alkenyl or alkinyl each having 3 to 7 carbon atoms, cycloalkyl having 5 to 7 carbon atoms which is optionally mono-substituted or disubstituted by identical or different fluorine, chlorine and/or methyl substituents, cycloalkylalkyl which has 3 to 7 carbon atoms in the cycloalkyl part and 1 to 4 carbon atoms in the alkyl part and is optionally monosubstituted or disubstituted by identical or different fluorine, chlorine and/or methyl substituents, or benzyl, it being possible for the phenyl part to be monosubstituted to trisubstituted by identical or different fluorine, chlorine, bromine, methyl, ethyl, n-propyl, tert.-butyl, methoxy, ethoxy, methylthio, ethylthio, trifluoromethyl, trifluoromethoxy, trifluoromethylthio, trifluoromethylsulphinyl, trifluoromethylsulphonyl, nitro, cyano, methoxycarbonyl, ethoxycarbonyl, phenyl which is optionally substituted by fluorine and/or chlorine, and/or phenoxy which is optionally substituted by fluorine and/or chlorine, or by two adjacent substituents which together represent a grouping of the formula

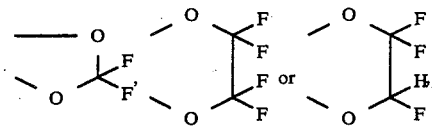

where $R^3$ represents trifluoromethoxy, however, when $R^4$ represents fluorine, chlorine or bromine.

Preferred compounds according to the invention are also addition products of acids and of those 1,4-disubstituted 1-azolyl-3,3-dimethyl-butane derivatives of the formula (I) in which the substituents $R^1$, $R^2$, $R^3$, $R^4$, $R^5$, $R^6$, $R^7$, A and Z have the meanings which have already been mentioned as preferable for these substituents.

The acids which can be adducted preferably include hydrohalic acids such as, for example, hydrochloric acid and hydrobromic acid, in particular hydrochloric acid, and furthermore phosphoric acid, nitric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, sulphonic acids such as, for example, p-toluenesulphonic acid and 1,5-naphthalenedisulphonic acid and also saccharin and thiosaccharin.

In addition, preferred compounds according to the invention are addition products of salts of metals of the main groups II to IV and the sub-groups I and II and also to VIII of the periodic table of the elements and of those compounds of the formula (I) in which the substituents $R^1$, $R^2$, $R^3$, $R^4$, $R^5$, $R^6$, $R^7$, A and Z have the meanings which have already been mentioned as preferable for substituents.

Salts Df copper, zinc, manganese, magnesium, tin, iron and nickel are particularly preferred here. Possible anions of these salts are those which are derived from those acids which lead to physiologically acceptable addition products. In this connection, particularly preferred acids of this type are hydrohalic acids such as, for example, hydrochloric acid and hydrobromic acid, and furthermore phosphoric acid, nitric acid and sulphuric acid.

The following compounds of the formula

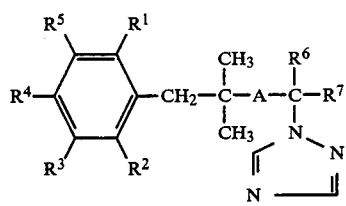

in which
A represents a keto group or a CH(OH) grouping and
Z represents a nitrogen atom or the CH group, may be mentioned individually in addition to the compounds mentioned in the preparation examples:

TABLE 1

| $R^1$ | $R^2$ | $R^3$ | $R^4$ | $R^5$ | $R^6$ | $R^7$ |
|---|---|---|---|---|---|---|
| H | H | Cl | $-OCF_3$ | H | H | $-CH_2-C\equiv CH$ |
| H | H | Cl | $-OCF_3$ | H | H | $-CH_2-\phi-Cl$ |
| H | H | Cl | $-OCF_3$ | H | H | $-CH_2-\phi$ |
| H | H | Cl | $-OCF_2Cl$ | H | H | $-CH_3$ |
| H | H | Cl | $-OCF_2Cl$ | H | H | $-C_2H_5$ |
| H | H | Cl | $-OCF_2Cl$ | H | H | $-C_3H_7$-n |
| H | H | Cl | $-OCF_2Cl$ | H | H | $-C_4H_9$ |
| H | H | Cl | $-OCF_2Cl$ | H | H | $-CH_2-CH=CH_2$ |
| H | H | Cl | $-OCF_2Cl$ | H | H | $-CH_2-C\equiv CH$ |
| H | H | Cl | $-OCF_2Cl$ | H | H | $-CH_2-\phi-Cl$ |
| H | H | Cl | $-OCF_2Cl$ | H | H | $-CH_2-\phi$ |
| H | H | F | $-OCF_3$ | H | H | $-CH_3$ |
| H | Cl | H | $-OCF_3$ | H | H | $-CH_2-CH=CH_2$ |
| H | F | H | $-OCF_3$ | H | H | $-CH_3$ |
| H | F | H | $-OCF_3$ | H | H | $-CH_2-CH=CH_2$ |
| H | H | H | $-OCHF_2$ | H | H | $-C_2H_5$ |
| H | H | H | $-OCHF_2$ | H | H | $-C_3H_7$-n |
| H | H | H | $-OCF_2CHF_2$ | H | H | $-CH_3$ |
| H | Cl | H | $-OCF_2CHF_2$ | H | H | $-CH_3$ |
| H | F | H | $-OCF_2CHF_2$ | H | H | $-CH_3$ |
| H | H | Cl | $-OCF_2CHF_2$ | H | H | $-CH_3$ |
| H | H | F | $-OCF_2CHF_2$ | H | H | $-CH_3$ |
| H | H | H | $-OCF_2CHF_2$ | H | H | $-C_2H_5$ |
| H | H | H | $-OCF_2CHF_2$ | H | H | $-C_3H_7$-n |
| H | H | H | $-OCF_2CHF_2$ | H | H | $-C_4H_9$-n |
| H | H | H | $-OCF_2CHF_2$ | H | H | $-CH_2-CH=CH_2$ |
| H | H | H | $-OCF_2CHF_2$ | H | H | $-CH_2-C\equiv CH$ |
| H | H | H | $-OCF_2CHF_2$ | H | H | $-CH_2-CH=CH-CH_3$ |
| H | H | H | $-OCF_2CHF_2$ | H | H | $-CH_2-C(CH_3)=CH_2$ |
| H | H | H | $-OCF_2CHFCl$ | H | H | $-CH_3$ |
| H | H | H | $-OCF_2CHFCl$ | H | H | $-CH_2-CH=CH-CH_3$ |
| H | H | Cl | $-OCF_2CHFCl$ | H | H | $-CH_3$ |
| H | H | H | $-OCH_2CF_3$ | H | H | $-CH_3$ |
| H | H | Cl | $-SCHF_2$ | H | H | $-CH_3$ |
| H | H | H | $-SCHF_2$ | H | H | $-CH_3$ |
| H | H | H | $-SCF_2CHFCl$ | H | H | $-CH_3$ |
| H | H | H | $-SCF_2CHF_2$ | H | H | $-CH_3$ |
| H | H | H | $-SCF_3$ | H | H | $-C_2H_5$ |
| H | H | H | $-SCF_3$ | H | H | $-C_3H_7$-n |
| H | H | H | $-SCF_3$ | H | H | $-C_4H_9$-n |
| H | H | H | $-SCF_3$ | H | H | $-CH_2-CH=CH_2$ |
| H | H | H | $-SCF_3$ | H | H | $-CH_2-CH=CH-CH_3$ |
| H | H | H | $-SCF_3$ | H | H | $-CH_2-C(CH_3)=CH_2$ |
| H | H | H | $-SCF_3$ | H | H | $-CH_2-\phi-Cl$ |
| H | H | H | $-SCF_3$ | H | H | $-CH_2-\phi$ |
| H | H | Cl | $-SCF_3$ | H | H | $-CH_3$ |
| H | H | Cl | $-SOCHF_2$ | H | H | $-CH_3$ |
| H | H | H | $-SOCHF_2$ | H | H | $-CH_3$ |
| H | H | H | $-SOCF_2CHFCl$ | H | H | $-CH_3$ |
| H | H | H | $-SOCF_2CHF_2$ | H | H | $-CH_3$ |
| H | H | H | $-SOCF_3$ | H | H | $-C_2H_5$ |
| H | H | H | $-SOCF_3$ | H | H | $-C_3H_7$-n |
| H | H | H | $-SOCF_3$ | H | H | $-C_4H_9$-n |
| H | H | H | $-SOCF_3$ | H | H | $-CH_2-CH=CH_2$ |
| H | H | H | $-SOCF_3$ | H | H | $-CH_2-CH=CH-CH_3$ |
| H | H | H | $-SOCF_3$ | H | H | $-CH_2-C(CH_3)=CH_2$ |
| H | H | H | $-SOCF_3$ | H | H | $-CH_2-\phi-Cl$ |
| H | H | H | $-SOCF_3$ | H | H | $-CH_2-\phi$ |
| H | H | Cl | $-SOCF_3$ | H | H | $-CH_3$ |
| H | H | Cl | $-SO_2CHF_2$ | H | H | $-CH_3$ |
| H | H | H | $-SO_2CHF_2$ | H | H | $-CH_3$ |
| H | H | H | $-SO_2CF_2CHFCl$ | H | H | $-CH_3$ |
| H | H | H | $-SO_2CF_2CHF_2$ | H | H | $-CH_3$ |
| H | H | H | $-SO_2CF_3$ | H | H | $-C_2H_5$ |
| H | H | H | $-SO_2CF_3$ | H | H | $-C_3H_7$-n |
| H | H | H | $-SO_2CF_3$ | H | H | $-C_4H_9$-n |
| H | H | H | $-SO_2CF_3$ | H | H | $-CH_2-CH=CH_2$ |
| H | H | H | $-SO_2CF_3$ | H | H | $-CH_2-CH=CH-CH_3$ |
| H | H | H | $-SO_2CF_3$ | H | H | $-CH_2-C(CH_3)=CH_2$ |

TABLE 1-continued

| R¹ | R² | R³ | R⁴ | R⁵ | R⁶ | R⁷ |
|----|----|----|----|----|----|----|
| H | H | H | —SO₂CF₃ | H | H | —CH₂—C₆H₄—Cl |
| H | H | H | —SO₂CF₃ | H | H | —CH₂—C₆H₅ |
| H | H | Cl | —SO₂CF₃ | H | H | —CH₃ |
| H | H | H | —O—CF₂—O— (fused, CF₂) | H |  | —CH₃ |
| H | H | H | —O—CF₂—O— (fused, CF₂) | H |  | —C₂H₅ |
| H | H | H | —O—CF₂—O— (fused, CF₂) | H |  | —C₃H₇-n |
| H | H | H | —O—CF₂—O— (fused, CF₂) | H |  | —CH₂—CH=CH₂ |
| H | H | H | —O—CF₂—O— (fused, CF₂) | H |  | —CH₂—CH=CH—CH₃ |
| H | H | Br | —OCF₃ | H | H | —CH₃ |
| H | H | Br | —OCF₃ | H | H | —C₂H₅ |
| H | H | Br | —OCF₃ | H | H | —C₃H₇-n |
| H | H | Br | —OCF₃ | H | H | —C₄H₉-n |
| H | H | Br | —OCF₃ | H | H | —CH₂—CH=CH₂ |
| H | H | Br | —OCF₃ | H | H | —CH₂—C≡CH |
| H | H | Br | —OCF₃ | H | H | —CH₂—C(CH₃)=CH₂ |
| H | H | Br | —OCF₃ | H | H | —CH₂—CH=CH—CH₃ |
| H | H | H | —O—CF₂—CF₂—O— (fused) | H |  | —CH₃ |
| H | H | H | —O—CF₂—CF₂—O— (fused) | H |  | —C₂H₅ |
| H | H | H | —O—CF₂—CF₂—O— (fused) | H |  | —C₃H₇-n |
| H | H | H | —O—CF₂—CF₂—O— (fused) | H |  | —C₄H₉-n |
| H | H | H | —O—CF₂—CF₂—O— (fused) | H |  | —CH₂—CH=CH₂ |
| H | H | H | —O—CF₂—CF₂—O— (fused) | H |  | —CH₂—CH=CH—CH₃ |
| H | H | H | —O—CF₂—CF₂—O— (fused) | H |  | —CH₂—C(CH₃)=CH₂ |
| H | H | H | —SCF₃ | H | CH₃ | —CH₃ |
| H | H | H | —SOCF₃ | H | CH₃ | —CH₃ |
| H | H | H | —SO₂CF₃ | H | CH₃ | —CH₃ |
| H | H | Cl | —OCF₃ | H | CH₃ | —CH₃ |
| H | H | Br | —OCF₃ | H | CH₃ | —CH₃ |
| H | H | H | —OCF₂Cl | H | CH₃ | —CH₃ |
| H | H | H | —SCF₂Cl | H | CH₃ | —CH₃ |
| H | H | H | —SOCF₂Cl | H | CH₃ | —CH₃ |
| H | H | H | —SO₂CF₂Cl | H | CH₃ | —CH₃ |
| H | H | H | —SCF₂Br | H | H | —CH₃ |
| H | H | H | —SOCF₂Br | H | H | —CH₃ |
| H | H | H | —SO₂CF₂Br | H | H | —CH₃ |
| H | H | H | —SCF₂Br | H | CH₃ | —CH₃ |
| H | H | H | —SOCF₂Br | H | CH₃ | —CH₃ |
| H | H | H | —SO₂CF₂Br | H | CH₃ | —CH₃ |
| H | H | H | —O—CF₂—O— (fused, CF₂) |  | CH₃ | —CH₃ |
| H | H | H | —O—CF₂—O— (fused, CF₂) |  | CH₃ | —CH₃ |
| H | H | H | —O—CF₂—CF₂—O— (fused) |  | CH₃ | —CH₃ |
| H | H | Cl | —OCF₂Cl | H | CH₃ | —CH₃ |
| H | H | H | —OCHF₂ | H | CH₃ | —CH₃ |
| H | H | H | —OCF₂CHF₂ | H | CH₃ | —CH₃ |
| H | H | H | —OCF₂CHFCl | H | CH₃ | —CH₃ |
| H | H | H | —SCHF₂ | H | CH₃ | —CH₃ |
| H | H | H | —SOCHF₂ | H | CH₃ | —CH₃ |
| H | H | H | —SO₂CHF₂ | H | CH₃ | —CH₃ |
| H | H | H | —SCF₂CHF₂ | H | CH₃ | —CH₃ |
| H | H | H | —SOCF₂CHF₂ | H | CH₃ | —CH₃ |
| H | H | H | —SO₂CF₂CHF₂ | H | CH₃ | —CH₃ |
| H | H | H | —SCF₂CHFCl | H | CH₃ | —CH₃ |
| H | H | H | —SOCF₂CHFCl | H | CH₃ | —CH₃ |
| H | H | H | —SO₂CF₂CHFCl | H | CH₃ | —CH₃ |
| H | F | H | —O—CF₂—O— (fused, CF₂) | H |  | —CH₃ |
| H | Cl | H | —O—CF₂—O— (fused, CF₂) | H |  | —C₂H₅ |

TABLE 1-continued

| $R^1$ $R^2$ $R^3$ | $R^4$ | $R^5$ | $R^6$ | $R^7$ |
|---|---|---|---|---|
| H F H | 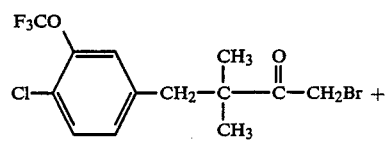 | | $CH_3$ | $-CH_3$ |
| H Cl H | | | $CH_3$ | $-CH_3$ |
| H Cl H | | | $CH_3$ | $-CH_3$ |
| H F H | | | H | $-CH_3$ |
| H Cl H | | | H | $-C_2H_5$ |

If, for example, 1-bromo-4-(4-chloro-3-trifluoromethoxyphenyl)-3,3-dimethyl-butan-2-one and 1,2,4-triazole are used as starting materials, then the course of process (a) according to the invention can be represented by the following equation:

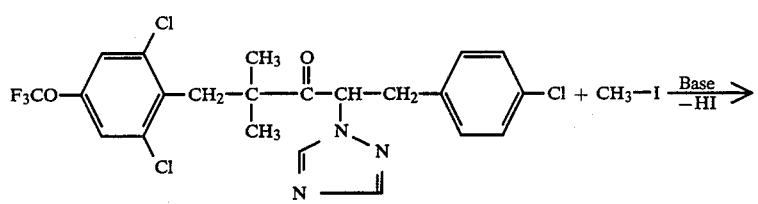

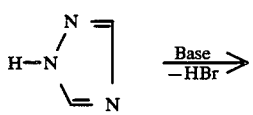

-continued

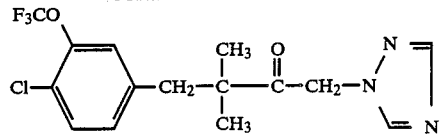

If, for example, 4-(2,6-dichloro-4-trifluoromethoxyphenyl)-3,3-dimethyl-1-(1,2,4-triazol-1-yl)-butan-2-one and 4-chloro-benzyl chloride are used as starting materials, then the course of process (b) according to the invention can be represented by the following equation:

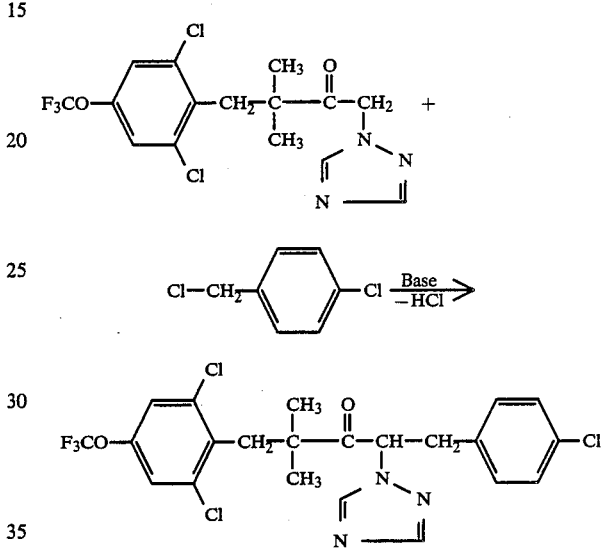

If, for example, 5-(2,6-dichloro-4-trifluoromethoxyphenyl)-1-(4-chlorophenyl)-4,4-dimethyl-2-(1,2,4-triazol-1-yl)-pentan-3-one and methyl iodide are used as starting materials, then the course of process (c) according to the invention can be represented by the following equation:

If, for example, 5-(2,6-dichloro-4-trifluoromethoxyphenyl)-1-(4-chlorophenyl)-2,4,4-trimethyl-2-(1,2,4-triazol-1-yl)-pentan-3-one is used as starting material and sodium borohydride as reductant, then the course of process (d) according to the invention can be represented by the following equation:

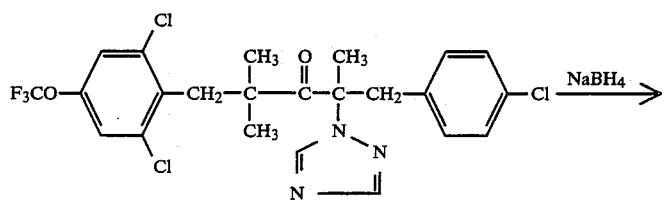

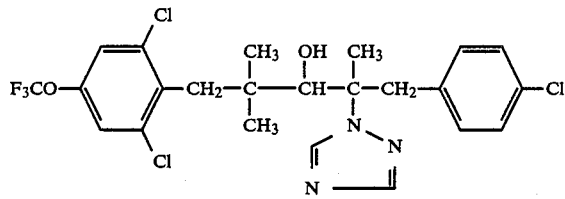

If, for example, 5-(2-chloro-4-trifluoromethylthiophenyl)-4,4-dimethyl-2-(1,2,4-triazol-1-yl)-pentan-3-one is used as starting material and hydrogen peroxide as oxidant, then the course of process (e) according to the invention can be represented by the following equation:

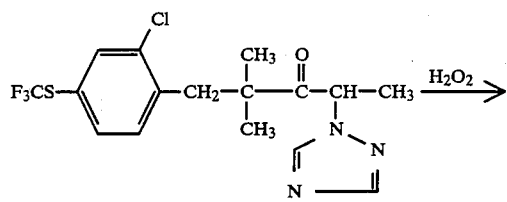

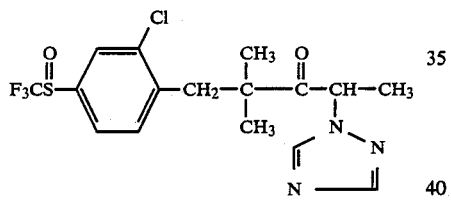

Formula (II) provides a general definition of the halogeno-ketones required as starting materials when carrying out process (a) according to the invention. In this formula, $R^1$, $R^2$, $R^3$, $R^4$ and $R^5$ preferably have those meanings which have already been mentioned as preferable for these radicals in connection with the description of the substances of the formula (I) according to the invention. Hal preferably represents chlorine, bromine or iodine.

Some of the halogenoketones of the formula (II) are known (compare DE-OS (German Published Specification) No. 3,048,266). They can be prepared by reacting ketones of the formula

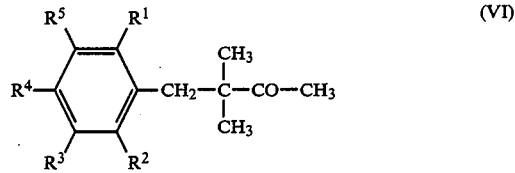

in which
$R^1$, $R^2$, $R^3$, $R^4$ and $R^5$ have the abovementioned meaning,
with chlorine or bromine in the presence of an inert organic solvent, such as, for example, ether, chlorinated or unchlorinated hydrocarbons, at room temperature, or with customary chlorinating agents, such as, for example, sulphuryl chloride, at temperatures between 20° C. and 60° C. The chloro and bromo ketones can be converted into the corresponding iodo compounds by customary processes.

Some of the ketones of the formula (VI) are known (compare DE-OS (German Published Specification) No. 3,048,266 and DE-OS (German Published Specification) No. 3,210,725). They can be obtained by reacting methyl isopropyl ketone with halogeno compounds of the formula

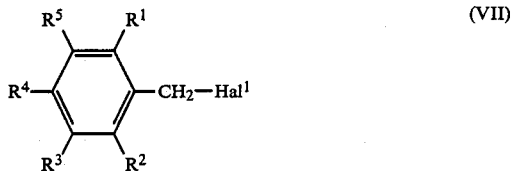

in which
$R^1$, $R^2$, $R^3$, $R^4$ and $R^5$ have the abovementioned meaning and
$Hal^1$ represents halogen, such as chlorine or bromine, in the presence of a base, such as, for example, an alkali metal hydroxide or an alkaline earth metal hydroxide, such as powdered potassium hydroxide and sodium hydroxide, and in the presence of a diluent, such as, for example, a (cyclo)aliphatic, optionally chlorinated aromatic hydrocarbon, such as benzene, xylene, chlorobenzene, dichlorobenzene, cyclohexane, petroleum ether, pentane, hexane or toluene, and also in the presence of a phase transfer catalyst, such as, for example, a derivative of ammonium salts, such as triethylbenzylammonium chloride, tetrabutylammonium iodide, tetrabutylammonium bromide or tetrabutylammonium chloride, at temperatures between 0° C. and 150° C.

Methyl isopropyl ketone and the halogeno compounds of the formula (VII) are generally known compounds of organic chemistry.

The azoles of the formula (III) to be used additionally as starting materials for process (a) according to the invention are likewise generally known compounds of organic chemistry.

For carrying out process (a) according to the invention, suitable diluents are inert organic solvents. These preferably include ketones, such as diethyl ketone, acetone and methyl ethyl ketone, nitriles, such as propionitrile and acetonitrile, alcohols, such as ethanol or isopropanol, ethers, such as tetrahydrofuran or dioxane, aromatic hydrocarbons, such as toluene, benzene or chlorobenzene, formamides, such as dimethylformamide, and halogenated hydrocarbons.

Acid-binding agents which are suitable for carrying out process (a) according to the invention are all customary inorganic and organic acid acceptors. Alkali metal carbonates, such as sodium carbonate, potassium carbonate and sodium hydrogen carbonate, and furthermore lower tertiary alkylamines, cycloalkylamines or aralkylamines, such as triethylamine, N,N-dimethylcyclohexylamine, dicyclohexylamine, N,N-dimethylbenzylamine, and furthermore pyridine and diazabicyclooctane may preferably be used. An excess of azole may also preferably be used.

The reaction temperatures can be varied within a substantial range when carrying out process (a) according to the invention. In general, the reaction is carried out between 20° C. and 150° C., preferably between 40° C. and 120° C.

When carrying out process (a) according to the invention, 2 to 4 mols of azole of the formula (III) and 1 to 4 mols of acid binder are preferably employed per mol of halogenoketone of the formula (II). The compounds of the formula (I) are isolated by customary methods. In general, a procedure is used in which the solvent is removed by distillation and the residue is worked up in a customary manner.

The compounds of the formula (Ia) required as starting materials for carrying out process (b) according to the invention are compounds according to the invention, which are obtainable by process (a).

Formula (IV) provides a general definition of the compounds additionally to be used as starting materials for process (b) according to the invention. In this formula, $R^8$ preferably represents those radicals which have already been mentioned as preferred for $R^6$ in connection with the description of the substances of the formula (I) according to the invention, excluding hydrogen. Y preferably represents chlorine, bromine, iodine, p-methylphenylsulphonyloxy, the grouping —O—SO$_2$—OR or NR$_3$, where R represents methyl, ethyl, n- or i-propyl.

The compounds of the formula (IV) are generally known substances of organic chemistry.

Suitable diluents for process (b) according to the invention are inert organic solvents. Aromatic hydrocarbons, such as benzene, toluene or xylene, halogenated hydrocarbons, such as methylene chloride, carbon tetrachloride, chloroform or chlorobenzene, esters, such as ethyl acetate, formamides, such as dimethylformamide, and also dimethyl sulphoxide may preferably be used.

Process (b) according to the invention is generally carried out in the presence of an acid-binding agent. All customary organic and, in particular, inorganic bases can be employed here. Alkali metal hydroxides or alkali metal carbonates, such as sodium hydroxide and potassium hydroxide, sodium carbonate and potassium carbonate may preferably be used.

The reaction temperatures can be varied within a substantial range when carrying out process (b) according to the invention. In general, the reaction is carried out at temperatures between 0° C. and 120° C., preferably between 20° C. and 100° C.

When carrying out process (b) according to the invention, 1 to 3.0 mols, preferably 1.5 to 2.0 mols of a compound of the formula (IV) are preferably employed per mol of a compound of the formula (Ia). The final products of the formula (I) are isolated by customary methods.

Process (b) according to the invention can also be carried out in a two-phase system, such as, for example, a system of aqueous sodium hydroxide solution or potassium hydroxide solution/toluene or methylene chloride, if desired with the addition of 0.1 to 1 mol of a phase-transfer catalyst, for example an ammonium or phosphonium compound, such as benzyldodecyldimethylammonium chloride or triethyl-benzyl-ammonium chloride.

The azolylketones of the formula (Ib) required as starting materials in process (c) are compounds according to the invention, which are obtainable by process (b). In this formula, $R^1$, $R^2$, $R^3$, $R^4$, $R^5$ and Z preferably have those meanings which have already been mentioned as preferred in connection with the description of the substances of the formula (I) according to the invention, and $R^8$ preferably has the meaning which has preferably been given for $R^6$ in the description of the substances of the formula (I) according to the invention, excluding hydrogen.

Formula (V) provides a general definition of the compounds to be additionally used as starting materials for process (c) according to the invention. In this formula, $R^9$ preferably represents those radicals which have already been mentioned as preferable for $R^7$ in connection with the description of the substances of the formula (I) according to the invention, excluding hydrogen. $Y^1$ preferably represents chlorine, bromine, iodine, p-methylphenylsulphonyloxy, the grouping —O—SO$_2$—OR or NR$_3$, where R represents methyl, ethyl, n- or i-propyl.

The compounds of the formula (V) are generally known substances of organic chemistry.

Process (c) according to the invention is carried out under the conditions which are also used in the case of process (b) according to the invention.

Formula (Ic) provides a definition of the compounds required as starting materials when carrying out process (d) according to the invention. These substances can be prepared by processes (a), (b) and (c) according to the invention.

The reduction according to the invention by process (d) is carried out by customary methods, for example by reaction of compounds of the formula (Ic) with complex hydrides, if appropriate in the presence of a diluent, or with aluminum isopropylate in the presence of a diluent.

Suitable complex hydrides are preferably sodium borohydride and lithium aluminum hydride.

If the reaction is carried out with complex hydrides, suitable diluents for the reaction according to the invention by process (d) are polar organic solvents. Alcohols, such as methanol, ethanol, butanol, isopropanol and ethers, such as diethyl ether or tetrahydrofuran may preferably be used.

The reduction with complex hydrides is generally carried out at temperatures between 0° C. and 30° C., preferably between 0° C. and 20° C. For this, about 1 mol of a complex hydride, such as sodium borohydride or lithium alanate are employed per mol of a ketone of the formula (Ic). To isolate the reduced compounds of the formula (I), the residue is taken up in dilute acid, for example hydrochloric acid, and the solution is then rendered alkaline and extracted with an organic solvent. Further working up takes place in a customary manner.

If the reaction is carried out using aluminum isopropylate in process (d) according to the invention, suitable diluents for the reaction are preferably alcohols, such as isopropanol, or inert hydrocarbons, such as benzene. The reaction temperatures can again be varied within a substantial range. In general, the reaction is carried out at temperatures between 20° C. and 120° C., preferably between 50° C. and 100° C. For carrying out the reaction, about 1 to 2 mols of aluminum isopropylate are employed per mol of a ketone of the formula (Ic). For isolating the reduced compounds of the formula (I), customary methods are used. In general, a procedure is used in which the excess solvent is removed by distillation under reduced pressure, and the resulting product is treated with dilute acid, such as sulphuric acid, or base, such as aqueous sodium hydroxide solution. Further working up takes place in a customary manner.

When carrying out processes (a) to (d) according to the invention, the reaction is generally carried out at atmospheric pressure. However, it is also possible to work at elevated or reduced pressure.

The compounds of the formula (Id) required as starting materials when carrying out process (e) according to the invention are substances according to the invention, which can be prepared by processes (a) to (d).

Suitable oxidants for carrying out process (e) customarily be used for sulphur oxidations. Hydrogen peroxide or organic peracids, such as for example, peracetic acid, 4-nitroperbenzoic acid or 3-chloroperbenzoic acid and also inorganic oxidants, such as periodic acid, potassium permanganate or chromic acid are preferably used.

Suitable diluents for carrying out process (e) according to the invention are inorganic or organic solvents, depending on the oxidant used. Alcohols, such as methanol or ethanol or their mixtures with water, and also pure water, acids, such as, for example, acetic acid, acetic anhydride or propionic acid or dipolar aprotic solvents, such as acetonitrile, acetone, ethyl acetate or dimethylformamide and also optionally halogenated hydrocarbons, such as benzine, benzene, toluene, hexane, cyclohexane, petroleum ether, dichloromethane, dichloroethane, chloroform, carbon tetrachloride or chlorobenzene are preferably used.

If desired, process (e) according to the invention can be carried out in the presence of an acid-binding agent. Those which are suitable are all customarily utilizable organic and inorganic acid-binding agents. Hydroxides, acetates or carbonates of alkaline earth metals or alkali metals, such as, for example, calcium hydroxide, sodium hydroxide, sodium acetate or sodium carbonate are preferably used.

If desired, process (e) according to the invention can be carried out in the presence of a suitable catalyst. Those which are suitable are all catalysts which may customarily be used for this type of sulphur oxidation. Heavy metal catalysts are preferably used; ammonium molybdate may be mentioned by way of example in this connection.

The reaction temperatures can be varied within a substantial range when carrying out process (e) according to the invention. In general, the reaction is carried out at temperatures between −30° C. and +100° C., preferably at temperatures between 0° C. and +80° C.

For carrying out process (e) according to the invention, 0.8 to 1.2 mols, preferably equimoar amounts, of oxidant are generally employed per mol of compounds of the formula (Id), when it is desired to interrupt the oxidation of the sulphur at the sulphoxide stage. For oxidation to the sulphone stage, 1.8 to 3.0 mols, preferably two-fold molar amounts, of oxidant are generally employed per mol of compounds of the formula (Id). The reaction is carried out and the sulphinyl or sulphonyl compounds of the formula (I) are worked up and isolated by generally known processes.

For the preparation of acid addition salts of the compounds of the formula (I), suitable acids are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the general formula (I) in a suitable inert solvent and adding the acid, for example hydrochloric acid, and can be isolated in a known manner, for example by filtering off, and if desired can be purified by washing with an inert organic solvent.

For the preparation of metal salt complexes of the compounds of the formula (I), suitable salts of metals are preferably those which have already been mentioned as preferred metal salts in connection with the description of the metal salt complexes according to the invention.

The metal salt complexes of compounds of the general formula (I) can be obtained in a simple manner by customary processes, thus, for example, by dissolving the metal salt in alcohol, for example ethanol, and adding the solution to compounds of the formula (I). Metal salt complexes can be isolated in a known manner, for example by filtering off, and can be purified by recrystallization, if necessary.

The active compounds according to the invention exhibit a strong microbicidal action and can be employed in practice for combating undesired microorganisms. The active compounds are suitable for use as plant protecting agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: *Xanthomonas* species, such as *Xanthomonas oryzae*; *Pseudomonas* species, such as *Pseudomonas lachrymans*; *Erwinia* species, such as *Erwinia amylovora*; *Pythium* species, such as *Pythium ultimum*; *Phytophthora* species, such as *Phytophthora infstans*; *Pseudoperonospora* species, such as *Pseudoperonospora humuli* or *Pseudoperonospora cubensis*; *Plasmopara* species, such as *Plasmopara viticola*; *Peronospora* species, such as *Peronospora pisi* or *P. brassicae*; *Erysiphe* species, such as *Erysiphe graminis*; *Sphaerotheca* species, such as *Sphaerotheca fuliginea*; *Podosphaera* species, such as *Podosphaera leucotricha*; *Venturia* species, such as *Venturia inaequalis*; *Pyrenophora* species, such as *Pyrenophora teres* or *P. graminea* (conidia form: Drechslera, syn: Helminthosporium); *Cochliobolus* species, such as *Cochliobolus sativus*; (conidia form: Drechslera, syn: Helminthosporium); *Uromyces* species, such as *Uromyces appendiculatus*; *Puccinia* species, such as *Puccinia recondita*; *Tilletia* species, such as *Tilletia caries*; *Ustilago* species, such as *Ustilago nuda* or *Ustilago avenae*; *Pellicularia* species, such as *Pellicularia sasakii*; *Pyricularia* species, such as *Pyricularia oryzae; Fusarium* species, such as *Fusarium culmorum; Botrytis* species, such as Botrytis cinerea; *Septoria* species, such as *Septoria nodorum; Leptosphaeria* species, such as *Leptosphaeria nodorum; Cercospora* species, such as *Cercospora canescens; Alternaria* species, such as *Alternaria brassicae* and *Pseudocercosporella* species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed here with particularly good success protectively for combating *Cochliobolus* species in barley, *Sphaerotheca* species in cucumbers, *Venturia* species in apples and *Pyricularia* species in rice and also as a seed treatment agent in wheat against *Fusarium culmorum*.

In addition, the active compounds according to the invention also possess a broad action against cereal diseases, in particular against mildew, rust, *Pseudocercosporella herpotrichoides, Septoria nodorum* and *Pyrenophora teres* as sprays and also against loose smut, leaf stripe and mildew as seed dressings. Furthermore, the active compounds according to the invention also show a good action against *Pellicularia sasakii* in rice in the in vitro test.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and into formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and also natural phospholipids, such as cephalins and lecithins and synthetic phospholipids can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, bactericides, insecticides, acaricides and herbicides, and also as mixtures with fertilizers and growth regulators.

The active compounds can be used as such, in the form of their formulations or in the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foamwat ing, brushing on and the like. It is furthermore possible to apply the active compounds by the ultra-low volume method, or to inject the active compound preparation or the active compound itself into the soil. The seed of the plants can also be treated.

When using the substances according to the invention as fungicides, the amounts employed can be varied within a substantial range, depending on the type of application. Thus, the active compound concentrations for treating parts of plants in the use forms are in general between 1 and 0.0001% by weight, preferably between 0.5 and 0.001%. In the treatment of seed, active compound amounts of 0.001 to 50 g per kilogram of seed, preferably 0.01 to 10 g, are generally required. When treating the soil, active compound concentrations of 0.00001 to 0.1% by weight, preferably 0.0001 to 0.02%, are required at the place of action.

The preparation and use of the active compounds according to the invention are shown in the following examples.

PREPARATION EXAMPLES

EXAMPLE 1

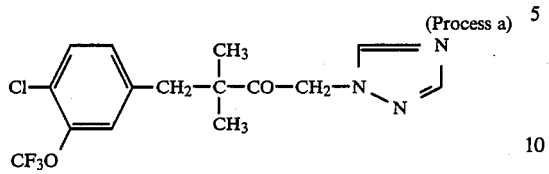
(Process a)

10.3 g (0.15 mol) of 1,2,4-triazole and 56.3 g (0.408 mol) of ground potassium carbonate are introduced into 300 ml of acetone. 50.8 g (0.136 mol) of 1-bromo-4-(4-chloro-3-trifluoro-methoxy-phenyl)-3,3-dimethyl- butan-2-one are added dropwise at 5° C.–10° C. After completion of the addition, the mixture is stirred at room temperature for 8 hours. For working up, the reaction mixture is filtered with suction and the filtrate is concentrated under reduced pressure. The residue is taken up in methylene chloride. The organic solution is washed with water, dried over sodium sulphate and concentrated under reduced pressure.

45.7 g (92.9% of theory) of 4-(4-chloro-3-trifluoromethoxy-phenyl)-3,3-dimethyl-1-(1,2,4-triazol-1-yl)-butan-2-one of refractive index $n_D^{20} = 1.5035$ are obtained.

Preparation of the starting compounds

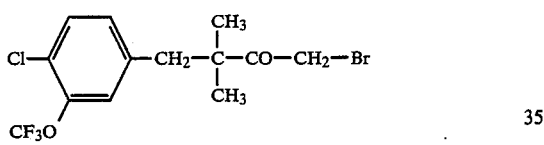

40 g (0.136 mol) of 4-(4-chloro-3-trifluoromethoxy-phenyl)-3,3-dimethyl-butan-2-one are dissolved in 130 ml of chloroform. 21.7 g (0.136 mol) of bromine are added dropwise with stirring at room temperature and the mixture is stirred for a further hour after completion of the addition. For working up, the mixture is concentrated under reduced pressure.

50.8 g (100% of theory) of 1-bromo-4-(4-chloro-trifluoromethoxy-phenyl)-3,3-dimethyl-butan-2-one of refractive index $n_D^{20} = 1.5015$ are obtained.

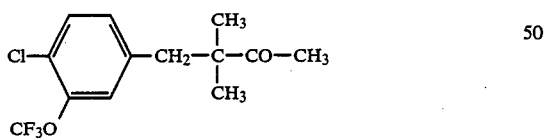

72.9 g (1.146 mols) of potassium hydroxide (powdered, 88% strength) and 3.8 g of tetrabutylammonium bromide are introduced into 100 ml of toluene. 39.4 g (0.458 mol) of methyl isopropyl ketone are added dropwise at room temperature with stirring and cooling. 93.7 g (0.382 mol) of 4-chloro-3-trifluoromethoxy-benzyl chloride are then added dropwise at 25° C. to 30° C. with stirring, and the mixture is stirred for a further 8 hours at room temperature. For working up, 200 ml of water are added to the reaction mixture and the phases are separated. The organic phase is dried and concentrated under reduced pressure. The residue is subjected to a fractional vacuum distillation.

35.8 g (31.8% of theory) of 4-(4-chloro-3-trifluoromethoxy-phenyl)-3,3-dimethyl-butan-2-one of boiling point 106° C.–110° C./0.1 mbar are obtained.

EXAMPLE 2

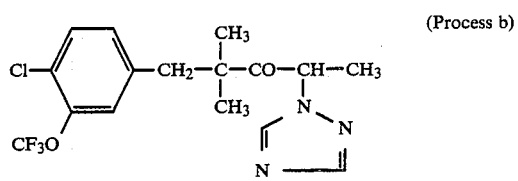
(Process b)

A solution of 23 g (0.064 mol) of 4-(4-chloro-3-trifluoromethoxy-phenyl)-3,3-dimethyl-1-(1,2,4-triazol-1-yl)-butan-2-one and 3.6 g (0.064 mol) of potassium hydroxide in 12 ml of water and 100 ml of dimethyl sulphoxide is introduced. 9.1 g (0.064 mol) of methyl iodide are introduced into the reaction mixture with stirring at room temperature, the temperature increasing to 55° C. The mixture is then stirred for a further 3 hours without heating. For working up, the reaction mixture is added to 600 ml of water. The mixture is extracted using methylene chloride, and the organic phase is washed twice with water, dried over sodium sulphate and concentrated under reduced pressure. The residue is purified by column chromatography on silica gel (eluent ethyl acetate/cyclohexane 3:1).

11.1 g (46.2% of theory) of 5-(4-chloro-3-trifluoromethoxy-phenyl)-4,4-dimethyl-2-(1,2,4-triazol-1-yl)-pentan-3-one of refractive index $n_D^{20} = 1.5004$ are obtained.

EXAMPLE 3

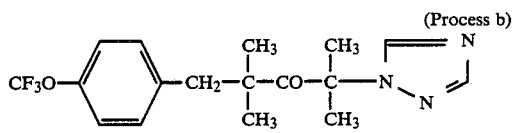
(Process b)

235.4 g (0.72 mol) of 4-(4-trifluoromethoxyphenyl)-3,3-dimethyl-1-(1,2,4-triazol-1-yl)-butan-2-one and 161.6 g (2.88 mols) of potassium hydroxide in 300 ml of water are introduced into 200 ml of dimethyl sulphoxide. 306.5 g (2.16 mols) of methyl iodide are added dropwise to the reaction mixture at 90° C. with stirring and the mixture is stirred for a further 3 hours at 90° C. The reaction mixture is then cooled to room temperature, added to water and extracted with dichloromethane. The organic phase is dried over sodium sulphate and concentrated under reduced pressure. The residue is purified by column chromatography on silica gel (eluant ethyl acetate/cyclohexane 3:1).

137.3 g (53.7% of theory) of 5-(4-trifluoromethoxyphenyl)-2,4,4-trimethyl-2-(1,2,4-triazol-1-yl)-pentan-3-one of melting point 100° C. are obtained.

EXAMPLE 4

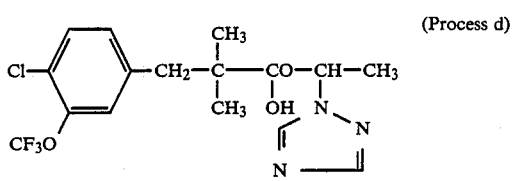
(Process d)

10 g (0.027 mol) of 5-(4-chloro-3-trifluoromethoxy-phenyl)-4,4-dimethyl-2-(1,2,4-triazol-1-yl)-pentan-3-one are introduced into 100 ml of methanol. A solution of 0.27 g (0.0073 mol) of sodium borohydride in 6 ml of water is added dropwise at room temperature. The reaction mixture is stirred for a further 2 hours at room temperature and concentrated under reduced pressure. The residue is taken up in dichloromethane. The organic phase is washed with water, dried over sodium sulphate and concentrated under reduced pressure. The crude product is recrystallized from petroleum ether.

7.65 g (75% of theory) of 5-(4-chloro-3-trifluoromethoxy-phenyl)-4,4-dimethyl-2-(1,2,4-triazol-1-yl)-pentan-3-ol of melting point 109° C.–110° C. are obtained.

The compounds shown below of the formula

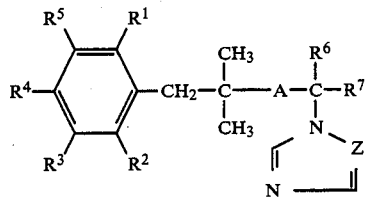

are obtained in an analogous manner to the methods described in Examples 1 to 4 and with regard to the instructions for processes (a) to (e) according to the invention:

| Example No. | $R^1$ | $R^2$ | $R^3$ | $R^4$ | $R^5$ | $R^6$ | $R^7$ | Z | A | Refractive index melting point |
|---|---|---|---|---|---|---|---|---|---|---|
| 5 | H | H | H | OCF$_2$Cl | H | H | H | N | —CO— | $n_D^{20}$ = 1.500 |
| 6 | H | H | H | OCF$_2$Cl | H | H | CH$_3$ | N | —CO— | $n_D^{20}$ = 1.505 |
| 7 | H | H | H | OCF$_2$Cl | H | H | CH$_3$ | N | —CH(OH)— | 82° C. |
| 8 | H | H | H | OCF$_3$ | Cl | H | H | N | —CO— | $n_D^{20}$ = 1.500 |
| 9 | H | H | H | OCF$_3$ | Cl | H | CH$_3$ | N | —CO— | $n_D^{20}$ = 1.500 |
| 10 | H | H | H | OCF$_3$ | Cl | H | CH$_3$ | N | —CH(OH)— | 75° C.–77° |
| 11 | H | H | H | OCF$_3$ | Cl | H | —CH$_2$—CH=CH$_2$ | N | —CO— | $n_D^{20}$ = 1.500 |
| 12 | H | H | H | OCF$_3$ | Cl | H | —CH$_2$—CH=CH$_2$ | N | —CH(OH)— | 68° C.–70° |
| 13 | H | H | H | OCF$_3$ | H | CH$_3$ | CH$_3$ | N | —CH(OH)— | 130° C. |
| 14 | H | H | Cl | OCF$_3$ | Cl | H | H | N | —CO— | $n_D^{20}$ = 1.5045 |
| 15 | H | H | Cl | OCF$_3$ | Cl | H | CH$_3$ | N | —CO— | $n_D^{20}$ = 1.5049 |
| 16 | H | H | Cl | OCF$_3$ | Cl | H | CH$_3$ | N | —CH(OH)— | 83° C.–85° C. |
| 17 | H | H | Cl | OCF$_2$CHClF | H | H | H | N | —CO— | $n_D^{20}$ = 1.5029 |
| 18 | Cl | H | H | SCF$_3$ | H | H | H | N | —CO— | $n_D^{20}$ = 1.5228 |
| 19 | H | H | (OCFH-CF$_2$-O cyclic) | | H | H | H | N | —CO— | $n_D^{20}$ = 1.5083 |
| 20 | Cl | H | H | SCF$_3$ | H | H | CH$_3$ | N | —CO— | $n_D^{20}$ = 1.5229 |
| 21 | H | H | (OCF$_2$-CFH-O cyclic) | | H | H | CH$_3$ | N | —CO— | $n_D^{20}$ = 1.5002 |
| 22 | Cl | H | H | SCF$_3$ | H | H | CH$_3$ | N | —CH(OH)— | $n_D^{20}$ = 1.5228 |
| 23 | H | H | (OCF$_2$-CFH-O cyclic) | | H | H | CH$_3$ | N | —CH(OH)— | 44° C.–46° C. |

-continued

| Example No. | $R^1$ | $R^2$ | $R^3$ | $R^4$ | $R^5$ | $R^6$ | $R^7$ | Z | A | Refractive index melting point |
|---|---|---|---|---|---|---|---|---|---|---|
| 24 | H | H | H | $SCF_3$ | H | H | H | N | —CH(OH)— | 78° C. |
| 25 | H | H | H | $OCF_3$ | H | H | H | N | —CH(OH)— | 105° C.–107° C. |
| 26 | H | H | H | $OCF_3$ | Cl | H | $CH_2$—C$_6$H$_4$—Cl | N | —CO— | 114° C. |
| 27 | H | H | H | $OCF_3$ | Cl | H | $CH_2$—CH=CH—$CH_3$ | N | —CO— | $n_D^{20} = 1.5010$ |
| 28 | H | H | H | $OCF_3$ | Cl | H | $CH_2$—C≡CH | N | —CO— | $n_D^{20} = 1.5067$ |
| 29 | H | H | H | $OCF_3$ | Cl | H | $CH_2$—C$_6$H$_{11}$ | N | —CO— | 92° C. |
| 30 | H | H | H | $OCHF_2$ | H | H | $CH_3$ | N | —CH(OH)— | $n_D^{20} = 1.5072$ |
| 31 | H | H | H | $OCF_3$ | Cl | H | $CH_2$—C$_6$H$_4$—Cl | N | —CH(OH)— | 141° C. |
| 32 | H | H | H | $OCF_3$ | Cl | H | —$C_3H_7$ | N | —CO— | $n_D^{20} = 1.4845$ |
| 33 | H | H | H | $OCHF_2$ | H | H | H | N | —CO— | $n_D^{20} = 1.5105$ |
| 34 | H | H | H | $OCHF_2$ | H | H | $CH_3$ | N | —CO— | $n_D^{20} = 1.5081$ |
| 35 | H | H | H | $OCF_3$ | Cl | H | —$C_3H_7$ | N | —CH(OH)— | 108° C. |
| 36 | H | H | H | $OCF_3$ | Cl | H | $CH_2$—C$_6$H$_{11}$ | N | —CH(OH)— | 129° C. |
| 37 | H | H | H | $OCF_3$ | Cl | H | $CH_2$—CH=CH—$CH_3$ | N | —CH(OH)— | 88° C. |
| 38 | H | H | H | $OCF_3$ | Cl | H | $CH_2$—C≡CH | N | —CH(OH)— | 112° C. |
| 39 | H | H | H | $OCF_3$ | Cl | $CH_3$ | $CH_2$—C$_6$H$_4$—Cl | N | —CO— | 110° C. |
| 40 | H | H | H | $OCF_3$ | Cl | $CH_3$ | $CH_2$—C$_6$H$_4$—Cl | N | —CH(OH)— | 80° C. |

USE EXAMPLES

The compounds given below were used as comparison substances in the following use examples:

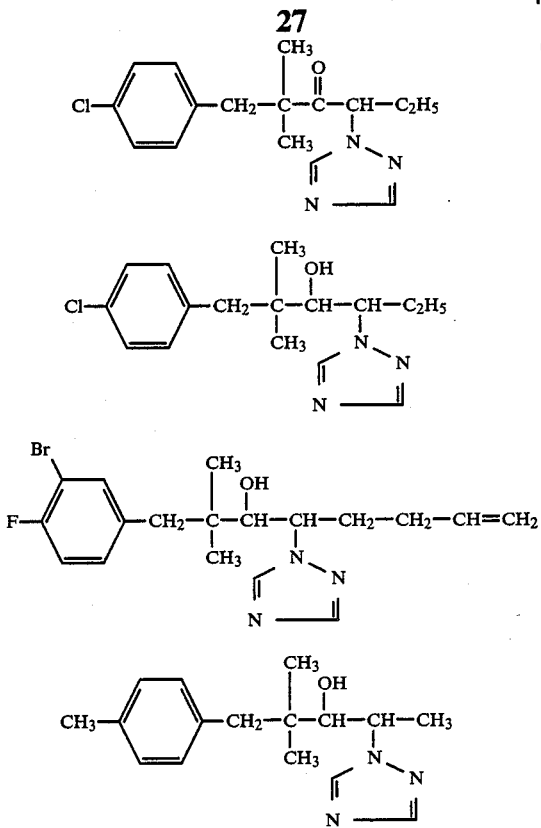

(The comparison substances (A), (B), (C) and (D) are known from U.S. Patent Specification 4,549,900).

EXAMPLE A

*Cochliobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compounds, according to the invention, shown in Examples (7), (10), (12) and (13) show a substantially better activity than the comparison substance (A).

EXAMPLE B

I Fusarium culmorum test wheat)/seed treatment
The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C., in seedboxes which are exposed to light for 15 hours daily.

About 3 weeks after sowing, the plants are evaluated for symptoms.

In this test, the compound, according to the invention, shown in Example (7) shows a substantially better activity than the comparison substance (B).

EXAMPLE C

*Sphaerotheca* test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, the compounds, according to the invention, shown in Examples (7), (10) and (12) show a substantially better activity than the comparison substances (A) and (D).

EXAMPLE D

*Venturia* test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compounds, according to the invention, shown in Examples (7), (10), (12) and (13) show a substantially better activity than the comparison substances (B) and (C).

EXAMPLE E

*Pyricularia* test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the compounds, according to the invention, shown in Examples (7), (10), (12) and (13) show a substantially better activity than the comparison substances (A) and (D).

It is understood that the specification and examples are illustrative but not limitative of the present invention and that other embodiments within the spirit and scope of the invention will suggest themselves to those skilled in the art.

We claim:

1. A 1,4-disubstituted 1-azolyl-3,3-dimethylbutane derivative of the formula

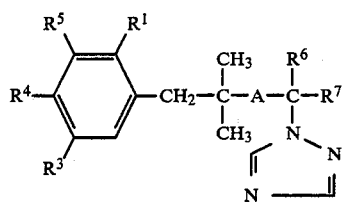

in which
R$^1$ represents hydrogen or chlorine,
R$^3$ represents hydrogen, chlorine or trifluoromethoxy,
R$^4$ represents chlorine, trifluoromethoxy, trifluoromethylthio, difluoromethoxy, difluorochloro-methoxy or trifluoro-chloroethoxy, or
R$^3$ and R$^4$ together represent the grouping of the formula

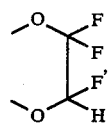

with the proviso that
R$^4$ can represent chlorine only if R$^3$ represents trifluoromethoxy,
R$^5$ represents hydrogen or chlorine,
A represents a keto group or a CH(OH) grouping,
R$^6$ represents hydrogen or methyl and
R$^7$ represents hydrogen, methyl, n-propyl, allyl, but-2-en-1-yl, propargyl, cyclohexylmethyl or 4-chloro-benzyl,
or an addition product thereof with an acid or metal salt.

2. A compound according to claim 1, wherein such compound is 5-(4-chlorodifluoromethoxyphenyl)-4,4-dimethyl-2-(1,2,4-triazol-1-yl)-pentan-3-ol of the formula

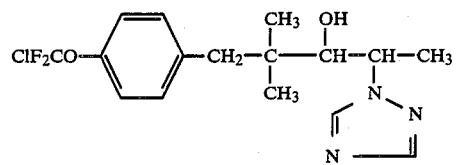

or an addition product thereof with an acid or metal salt.

3. A compound according to claim 1, wherein such compound is 5-(3-chloro-4-trifluoromethoxyphenyl)-4,4-dimethyl-2-(1,2,4-triazol-1-yl)-pentan-3-ol of the formula

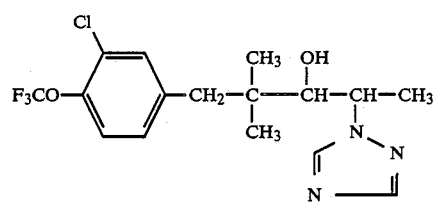

or an addition product thereof with an acid or metal salt.

4. A compound according to claim 1, wherein such compound is 7-(3-chloro-4-trifluoromethoxyphenyl)-6,6dimethyl-4-(1,2,4-triazol-1-yl)-hept-1-en-5-ol of the formula

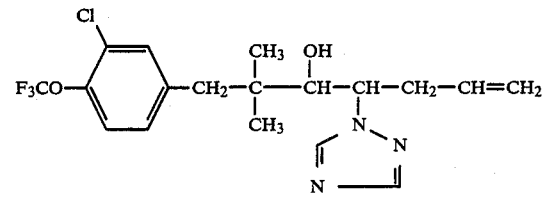

or an addition product thereof with an acid or metal salt.

5. A compound according to claim 1, wherein such compound is 5-(3-chloro-4-trifluoromethoxyphenyl)-2,4,4-trimethyl-3-(1,2,4-triazol-1-yl)-pentan-3-ol of the formula

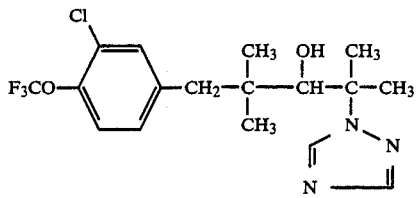

or an addition product thereof with an acid or metal salt.

6. A compound according to claim 1, wherein such comound is 5-(2,2,3-trifluoro-benzo-1,4-dioxan-7-yl)-4,4-dimethyl-2-(1,2,4-triazol-1-yl)-pentan-3-ol of the formula

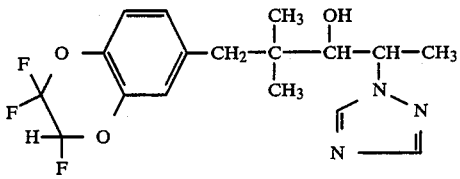

or an addition product thereof with an acid or metal salt.

7. A compound according to claim 1, wherein such compound is 5-(4-difluoromethoxyphenyl)-4,4-dimethyl-2-(1,2,4-triazol-1-yl)-pentan-3-ol of the formula

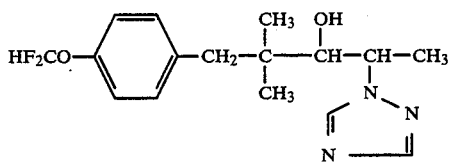

or an addition product thereof with an acid or metal salt.

8. A fungicidal composition comprising a fungicidally effective amount of a compound or addition product according to claim 1 and an inert diluent.

9. A method of combating fungi which comprises applying to such fungi or to a fungus habitat an amount effective therefor of a compound or addition product according to claim 1.

10. The method according to claim 9, wherein such compound is
5-(4-chlorodifluoromethoxyphenyl)-4,4-dimethyl-2-(1,2,4-triazol-1-yl) pentan-3-ol,
5-(3-chloro-4-trifluoromethoxyphenyl)-4,4-dimethyl-2-(1,2,4-triazol-1-yl)-pentan-3-ol,
7-(3-chloro-4-trifluoromethoxyphenyl)-6,6-dimethyl-4-(1,2,4-triazol-1-yl)-hept-1-en-5ol,
5-(3-chloro-4-trifluoromethoxyphenyl)-2,4,4-trimethyl-3-(1,2,4-triazol-1-yl)-pentan-3-ol,
5-(2,2,3-trifluoro-benzo-1,4-dioxan-7-yl)-4,4-dimethyl-2-(1,2,4-triazoly-1-yl)-pentan-3ol or
5-(4-difluoromethoxyphenyl)-4,4-dimethyl-2-(1,2,4-triazol-1-yl)-pentan-3-ol, or an addition product thereof with an acid or metal salt.

* * * * *

UNITED STATES PATENT AND TRADEMARK OFFICE
CERTIFICATE OF CORRECTION

PATENT NO. : 4,968,712

DATED : November 6, 1990

INVENTOR(S) : Elbe et al.

It is certified that error appears in the above-identified patent and that said Letters Patent is hereby corrected as shown below:

Title Page      ABSTRACT: Line 3 delete "  " and substitute

--  --

Col. 1, line 35    Delete "  " and substitute --  --

Signed and Sealed this

Twenty-fifth Day of August, 1992

*Attest:*

DOUGLAS B. COMER

*Attesting Officer*    *Acting Commissioner of Patents and Trademarks*